(12) United States Patent
Paproski et al.

(10) Patent No.: US 9,719,933 B1
(45) Date of Patent: Aug. 1, 2017

(54) LASER-INDUCED BREAKDOWN SPECTROSCOPY OF OIL SANDS

(71) Applicants: SYNCRUDE CANADA LTD. in trust for the owners of the Syncrude Project as such owners exist now and in the future, Fort McMurray (CA); NATIONAL RESEARCH COUNCIL OF CANADA, Ottawa (CA)

(72) Inventors: Richard Paproski, Edmonton (CA); Aïssa Harhira, Montreal (CA); David Duford, Edmonton (CA); Josette El Haddad, Boucherville (CA); Darcy Daugela, Edmonton (CA); Alain Blouin, Montreal (CA); Mohamad Sabsabi, Longueuil (CA)

(73) Assignees: SYNCRUDE CANADA LTD, Fort McMurray (CA), in trust for the owners of the Syncrude Project as such owners exist now and in the future; NATIONAL RESEARCH COUNCIL OF CANADA, Ottawa (CA)

(*) Notice: Subject to any disclaimer, the term of this patent is extended or adjusted under 35 U.S.C. 154(b) by 0 days.

(21) Appl. No.: 15/360,706

(22) Filed: Nov. 23, 2016

Related U.S. Application Data

(60) Provisional application No. 62/327,293, filed on Apr. 25, 2016.

(51) Int. Cl.
*G01J 3/30* (2006.01)
*G01N 21/71* (2006.01)
*G01N 33/24* (2006.01)

(52) U.S. Cl.
CPC .......... *G01N 21/718* (2013.01); *G01N 33/24* (2013.01); *G01N 2201/06113* (2013.01); *G01N 2201/127* (2013.01); *G01N 2201/129* (2013.01)

(58) Field of Classification Search
CPC ...... G01N 21/71; G01N 21/718; G01N 33/24; G01N 21/64; G01J 3/443; G01J 3/44
See application file for complete search history.

(56) References Cited

U.S. PATENT DOCUMENTS

2003/0234928 A1* 12/2003 Lucas ................. G01N 21/718
356/318
2016/0045841 A1 2/2016 Kaplan et al.

FOREIGN PATENT DOCUMENTS

CA 2931676 A1 6/2015

* cited by examiner

*Primary Examiner* — Abdullahi Nur
(74) *Attorney, Agent, or Firm* — Bennett Jones LLP

(57) ABSTRACT

A method of quantifying at least one property of interest of an oil sands ore sample is provided using a laser-induced breakdown spectroscopy (LIBS) method. The LIBS method may be applied to oil sands ore being conveyed prior to a slurry process to measure oil sand composition and provide information which may predict extraction characteristics. The LIBS method may be applied to oil sands core samples in a laboratory setting to reduce the cost and analysis time associated with conventional laboratory measurement techniques.

5 Claims, 20 Drawing Sheets

LASER-INDUCED BREAKDOWN SPECTROSCOPY OF OIL SANDS

FIELD OF THE INVENTION

This invention relates to systems and methods of characterizing oil sands ore using laser-induced breakdown spectroscopy.

BACKGROUND

Oil production from bituminous sand involves the basic steps of mining, bitumen extraction, bitumen froth treatment, and upgrading the bitumen to synthetic oil. Bitumen is commonly recovered from the surface-mined oil sands ore using a variation of the Clark Hot Water Extraction (CHWE) process. In this process, the ores are mined and then crushed for size reduction. Hot water is added to the ore to form a slurry, which is transported using a hydro-transport line to a primary separation vessel (PSV). Bitumen is recovered in the PSV by flotation of bitumen froth. The recovered bitumen froth may consist of about 60% bitumen, 10% solids and 30% water (by weight). The tailings materials from the PSV can be processed in a secondary flotation process to produce a secondary bitumen froth. The recovered bitumen froth can be sent to froth treatment vessels to reduce the water and solids content. Diluents (naphtha or paraffin solvents) are added and the diluted froth is heated to reduce the viscosity. At the end of the process, a mixture of clays, water, sand, and traces of unrecovered hydrocarbons combined with process chemicals, known as tailings, is pumped out to settling ponds and the recovered bitumen is sent to the upgrader.

Prior to the bitumen extraction process, and particularly prior to the recovery of bitumen by flotation, it is important that the oil sand feedstock be characterized and operating parameters be adjusted and controlled such that the percentage of bitumen recovered in the primary and secondary bitumen froths, and the quality of the recovered bitumen froths in terms of high bitumen, low water, and low solids content, is controlled within certain predetermined limits.

To achieve these goals, it is important to be able to measure the bitumen, water, and/or solids content in oil sand core samples in the laboratory, to help with mine planning, and oil sand ore samples on a conveyor belt, to monitor the feed material to help control the extraction process. It may also be important to be able to predict properties relating to the extraction characteristics (i.e. processability) of oil sand ores. As known in the art, Batch Extraction Units (BEU) [Sanford, E. C., Seyer, F. A., "Processability of Athabasca Tar Sand Using A Batch Extraction Unit: The Role of NaOH," Canadian Mining & Metallurgical Bulletin (CIM Magazine), Vol. 72, Issue 803, March 1979, 164-169.] can be used to measure the extraction characteristics of oil sand ore samples under different conditions in order to better understand process conditions and sample properties that result in high bitumen recovery and high bitumen froth quality.

Several processes in the oil sands production may benefit from online monitoring. However, oil sand ore samples often present difficulties, largely related to the heterogeneity of the samples, different particle sizes, several phases, wetted and covered particles, and the fact that surface composition may not be representative of the bulk composition.

The Dean-Stark extraction method is considered to be an accurate method for determining bitumen, water, and/or solids content of a sample. A weighed sample is separated into bitumen, water, and solids by refluxing toluene in a Soxhlet extraction apparatus. Condensed toluene and co-distilled water are continuously separated in a trap designed to recycle the solvent through the extraction thimble, dissolving the bitumen present in the sample, while the water is retained in the trap. Full extraction of bitumen from the solids can often take hours to complete. Once the three components have been physically separated, they can be quantified by various means. The clean and dry solids can be further analyzed by a variety of techniques, including particle size distribution by wet sieving or laser diffraction, methylene blue index titration, elemental analysis, and mineralogy by X-ray diffraction.

Given the long analysis time of Dean-Stark extraction, and the inability to perform many other conventional laboratory measurements on the solids without first removing the bitumen and water, faster laboratory methods are often used to monitor a continuous extraction train used for extracting bitumen from oil sand. These fast methods typically sacrifice accuracy and/or repeatability in order to achieve a shorter analysis time. They often rely on an extraction step, filtration step, centrifugation step, and/or drying step to separate various components prior to measurement, which adds to the total analysis time. Extraction process conditions can quickly change within minutes, making ever shorter analysis times desirable. Many laboratory measurements cannot be performed sufficiently fast either online or in a laboratory setting to be useful for monitoring an extraction process (e.g. methylene blue index titration, elemental analysis, X-ray diffraction, and BEU extraction processability characteristics).

Nuclear magnetic resonance (NMR) techniques for measuring bitumen, water, and solids (by-difference) are known but are limited in the type of information that they can provide, as known to those skilled in the art.

Near-infrared reflectance measurements and $^{40}$K radiation measurements have been used to estimate the oil sand ore bitumen and fine particle content online. While efforts continue to improve the accuracy, precision, and reliability of these tools, they also provide only limited information about the ore as known to those skilled in the art.

Therefore, there remains a need in the art for analytical methods which may permit online, real-time monitoring of oil sand composition and extraction characteristics. Preferably, the method may be faster for measuring the content of bitumen, water and solids, compared to Dean-Stark extraction, while maintaining satisfactory accuracy and precision. The method may also provide additional information about the samples that cannot be measured quickly (e.g. minutes) in a laboratory or online using conventional analytical techniques.

SUMMARY OF THE INVENTION

The present invention comprises a method of quantifying at least one property of interest of an oil sands sample using a laser-induced breakdown spectroscopy (LIBS) method. In one embodiment, the LIBS method may be applied to oil sands ore being conveyed prior to a slurry process to measure oil sand composition and provide information which may predict extraction characteristics. In another embodiment, the LIBS method may be applied to oil sands core samples in a laboratory setting to reduce the cost and analysis time associated with conventional laboratory measurement techniques.

A LIBS method may be advantageous in that sample preparation is typically not necessary. Laser focusing provides spatial resolution, allowing the study of distributions of sample properties throughout samples (e.g. with increasing geological depth along the linear length of a core sample). Moreover, the method can be applied to liquids and gases as well as to solids. Finally, contact with the sample is not necessary, and analysis can be made at a distance in harsh environments with the use of optical fibers or with the use of standoff techniques. In one embodiment, this method may be relatively simple to operate, produce results relatively quickly, may be automated, and may provide multi-facetted information in seconds.

In one aspect, the invention may comprise a method of determining at least one property of interest of a test oil sands ore sample, comprising the steps of:

(a) applying a plurality of pulsed laser shots focused on a surface of the test oil sands ore sample to ablate the test oil sands ore sample and create a plurality of short-lived plasmas;

(b) acquiring the emission spectra from at least some or all of the plasmas;

(c) repeating steps (a) and (b) on one or more ablation sites until a predetermined minimum ablation depth and volume have been achieved;

(d) averaging the acquired emission spectra together for the test oil sands ore sample to form a test emission spectrum;

(e) optionally, preprocessing the test emission spectrum;

(f) applying at least one calibration loading to determine the at least one property of interest, wherein the at least one calibration loading is obtained from a chemometric model relating an emission spectrum, or a portion of an emission spectrum, obtained from a known oil sands ore sample to a reference value obtained from a physicochemical analysis method for determining the at least one property of interest of the known oil sands ore sample.

In one embodiment, the minimum depth of each ablation site is about 4 mm, and the minimum total ablation volume from all ablation sites is about 0.3 $cm^3$.

In one embodiment, the at least one property of interest may comprise one or more of:

(1) properties related to oil sand bitumen extraction characteristic(s), comprising one or more of:
  a. Primary bitumen recovery
  b. Combined primary and secondary bitumen recovery
  c. Primary froth bitumen content
  d. Combined primary and secondary froth bitumen content
  e. Primary froth water content
  f. Combined primary and secondary froth water content
  g. Primary froth solids content
  h. Combined primary and secondary froth solids content
  i. Optimal process aid dosage (including but not limited to caustic); or (2) properties conventionally measured in a laboratory comprising either or both:
  j. Solids particle size information; or
  k. Solids methylene blue index.

In another aspect, the invention may comprise the use of a laser induced breakdown plasma spectroscopic system comprising a laser ablator and a detector combined with one or more processors and a memory, wherein the memory stores machine-readable instructions that, when executed by the one or more processors, cause the system to carry out functions to implement one of the methods described or claimed herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
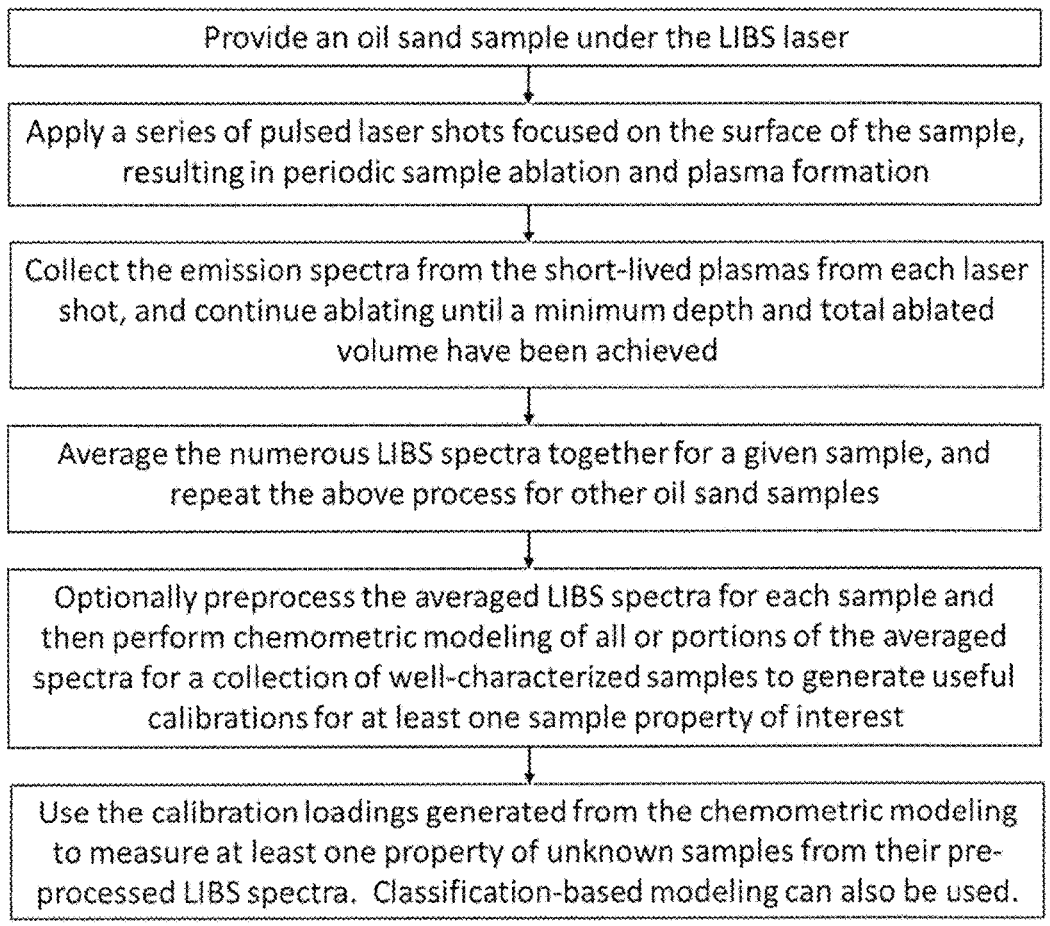
FIG. 1 shows a schematic flowchart of one embodiment of a method of the present invention.

In this description, certain terms have the meanings provided. All other terms and phrases used in this specification have their ordinary meanings as one of skilled in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

LIBS is a type of atomic emission spectroscopy that uses a laser as the excitation source. LIBS operates by focusing the laser onto an area on the surface of a target sample. When the pulsed laser is discharged it ablates a small amount of material and creates an ablation site and a plasma plume. The ablated material dissociates (i.e. breaks down) into excited ionic, atomic, and molecular fragment species. During this time, the plasma emits a continuum of radiation, and the plasma expands and cools. The characteristic emission lines of the elements and molecular fragments in the plasma can be observed at certain times following the initial ablation and plasma formation.

The term "plasma" refers to a plume of material that includes excited ions, atoms, molecular fragments, and electrons which is produced when a laser pulse of sufficient energy contacts the sample. The excited ionic, atomic, and molecular fragment species from the target sample may be representative of the composition and properties of the target sample. Spectroscopic analysis of detected emissions from the plasma can be used for characterization (e.g. chemical composition and properties) of the ablated sample material.

In one aspect, the invention comprises a method of determining at least one property of interest of a test oil sands ore sample, comprising the steps of:

(a) applying a plurality of pulsed laser shots focused on a surface of the test oil sands ore sample to ablate the test oil sands ore sample and create a plurality of short-lived plasmas;

(b) acquiring the emission spectra from at least some or all of the plasmas;

(c) repeating steps (a) and (b) on one or more ablation sites until a predetermined minimum ablation depth and total ablation volume have been achieved;

(d) averaging the acquired emission spectra together for the test oil sands ore sample to form a test emission spectrum;

(e) optionally, preprocessing the test emission spectrum;

(f) applying at least one calibration loading to determine the at least one property of interest, wherein the at least one calibration loading is obtained from a chemometric model relating an emission spectrum, or a portion of an emission spectrum, obtained from a known oil sands ore sample to a reference value obtained from a physicochemical analysis method for determining the at least one property of interest of the known oil sands ore sample; provided that the test or known oil sands ore sample is not an aqueous oil sands slurry.

In one embodiment, the at least one property of interest measured chemometrically from acquired LIBS spectra comprises one or more of the following:

(1) properties related to oil sand bitumen extraction characteristic(s), comprising one or more of:
  a. Primary bitumen recovery
  b. Combined primary and secondary bitumen recovery
  c. Primary froth bitumen content
  d. Combined primary and secondary froth bitumen content
  e. Primary froth water content
  f. Combined primary and secondary froth water content
  g. Primary froth solids content
  h. Combined primary and secondary froth solids content
  i. Optimal process aid dosage (including but not limited to caustic); or (2) properties conventionally measured in a lab comprising either or both:
  j. Solids particle size information; or
  k. Solids methylene blue index.

In one embodiment, the test emission spectrum is an averaged spectrum created from a plurality of spectra created from a plurality of lasers shots at the sample. For example, a pulsed laser may be used to ablate a very thin (e.g. on the order of microns) surface layer of the sample, resulting in a shallow crater. Up to thousands of pulsed laser shots may be used to ablate to a cumulative depth of 4 mm or more, while also collecting the emission spectrum from each short-lived plasma. Due to the heterogeneous nature of oil sand, where surface properties and surface component concentrations may not accurately represent bulk properties and compositions, LIBS sampling depth should be on the order of 4 mm or greater, with total ablated volumes on the order of 0.3 cm$^3$ or greater. The minimum total ablated volume may be achieved by laser sampling multiple positions across the sample surface provided that a minimum sampling depth is satisfied at each sampling position. This is to minimize sampling errors associated with solid particles of various particle sizes and surface-coated in various thicknesses of bitumen and/or water. The minimum sampling depth and volume may change according to sample characteristics.

In one embodiment, the test emission spectrum may be pre-processed by applying methods of normalization, weighting, noise-reduction, or other mathematical manipulations to produce a processed test emission spectrum that can be more readily modelled by chemometric methods. Pre-processing methods are well-known to those skilled in the art, and may be implemented with commercially available software products.

In one embodiment, the relevant chemical information for measuring the at least one oil sands property of interest may be concentrated in specific spectral regions of the emission spectra where the emission lines of certain elements and/or molecular fragments may be found. The test emission spectrum may be limited to those spectral regions, or combinations of those spectral regions.

As used herein, "oil sands ore" means an ore obtained from an oil sand deposit which generally comprises four distinct layers or zones: muskeg, overburden, oil sands ore and rock. Oil sands ore comprises bitumen-rich sand, fine clays and aquifer water. Samples of oil sands ore useful in the present invention can be obtained by conventional coring technologies or can be surface mined if the oil sands ore layer is close enough to the surface to be mined (normally less than about 50-75 meters below the surface). The oil sand ore sample can be accessed, processed, and/or presented to the LIBS system by various means (e.g. an oil sands core sample in a laboratory, in-situ via a hole drilled from the surface, an exposed surface mine face, ore on a conveyor). For further clarification, as used herein, "oil sands ore" does not include aqueous oil sands slurry.

As used herein, "physicochemical method" includes any laboratory method accepted by one skilled in the art as being reasonably accurate to either (i) quantify the amount of a component in, or (ii) determine a physical property of, an oil sands ore sample. Examples include, without limitation, bitumen, water, and solids content as measured by the Dean-Stark analysis method, particle size information as measured by laser diffraction or other means, methylene blue index as measured by titration or other means, elemental concentrations as measured by inductively coupled plasma optical emission spectrometry or other means, and extraction processability-related information including those listed above by operating an oil sands batch extraction unit under a given set of relevant conditions and analyzing the isolated primary froth, secondary froth, and tailings materials by Dean-Stark analysis. As used herein, a "known sample", a "well-characterized sample", or a "sample with known composition" is one that has been analyzed and quantified using one or more such physicochemical methods.

As used herein, "process aid" refers to chemicals added to oil sand ore to facilitate in the solvent extraction of bitumen therefrom. Examples of process aids include caustic (e.g., sodium hydroxide), sodium citrate, sodium silicate, sodium triphosphate, lime, borax, kerosene, diesel, or combinations thereof.

In one embodiment, the chemometric model comprises a calibration model produced by multivariate regression or pattern recognition methods of emission spectra of the training set of samples, which are of known composition. The chemometric model is built to describe the relationship between the properties of interest (concentrations and other properties) and the intensities of emission spectra collected from the plasma. Once a test emission spectrum has been obtained, the calibration loadings may be applied to it to produce a result. A calibration loading may comprise calibration values derived from signal intensities for a plurality of different wavelengths in the emission spectrum but may not necessarily include the entire collected emission spectrum.

Regression analysis and pattern recognition methods are well known in the art, and may be implemented using commercially available software products. Suitable methods include, without limitation, Support Vector Machine (SVM) methods, Principal Component Regression (PCR) methods, or Partial Least Squares Regression (PLSR). Chemometric classification methods may also be used to group oil sand samples into useful classes (e.g. primary BEU bitumen recovery under a given set of conditions >80%, 60-80%, 40-60%, or <40%) rather than attempting to predict their properties numerically (e.g. primary BEU bitumen recovery under a given set of conditions of 84%).

In another aspect, the invention may include the use of a laser induced breakdown plasma spectroscopic system comprising a laser ablator and a detector combined with one or more processors and a memory, wherein the memory stores machine-readable instructions that, when executed by the one or more processors, cause the system to carry out functions to implement the methods described or claimed herein.

In some cases, the ablator is configured to contact the target sample with a laser beam at a desired illumination angle with respect to the target surface. For example, the ablator may be configured to contact the surface of the target sample with a laser beam where the angle between the surface of the target sample and the laser beam ranges from 0 degrees to 90 degrees, such as 30 degrees, or 45 degrees, or 60 degrees. In certain embodiments, the ablator is configured to contact the surface of the target sample with a laser beam where the laser beam is substantially at right angles to the surface of the target sample.

Certain embodiments of the laser are configured to have a short pulse width. Lasers that have a short pulse width may be configured to have a high repetition rate, such that a plurality of laser pulses may be emitted within a given amount of time. In some cases, the laser is configured to have a repetition rate from 1 Hz up to 10 MHz. A laser having a short pulse width may facilitate an improvement in the signal-to-noise ratio for the device. For example, in some instances, the laser has a short pulse width, such as a pulse width that is shorter than the time it takes for the plasma to form at the ablation site after the laser beam contacts the target sample. In these cases, the laser beam, such as the trailing portion of the laser beam, may have a reduced time to interact with the plasma. In addition, the plasma may expand and disperse in three-dimensions away from the ablation site. As the plasma expands in three-dimensions away from the ablation site, this may also facilitate a reduction in the interaction of the laser beam with the plasma. In certain embodiments, a reduction in the interaction of the laser beam with the plasma facilitates a reduction in wide spectrum background noise in the detected emissions signals and thus facilitates an increase in the signal-to-noise ratio. Powerful and fast repetition rate pulsed lasers may be useful in achieving the minimum ablation depth for oil sand ore on a moving conveyor belt.

In certain embodiments, the laser may be a nanosecond laser having a pulse width on the order of nanoseconds. In another embodiment, the laser may be a femtosecond laser having a pulse width on the order of femtoseconds. In certain instances, the nanosecond laser is a Q-switched Nd:YAG laser. In certain instances, the femtosecond laser is a femtosecond fiber laser. In certain instances, femtosecond lasers may offer closer to stoichiometric sampling, reduced wide spectrum background emission, and shorter-lived plasmas which permit the use of higher repetition rate laser pulses.

In certain embodiments, the ablator includes an optical system configured to direct a laser beam from a laser source to a surface of a target sample.

In certain embodiments, the laser has a focal spot diameter ranging from 1 μm to 1 cm. The focal spot diameter is the diameter of the laser beam at its focal spot, and where the laser beam has the highest concentrated energy. The laser beam should be focused near or just below the surface of the sample for efficient sample ablation and plasma formation. Minimum thresholds for energy delivered per unit time over a given area must be achieved for efficient sample ablation and plasma formation.

In certain embodiments, the subject LIBS device includes a detector. The detector may be configured to detect emissions from the plasma produced at the surface of the target sample by the ablator. For example, the detector may be configured to detect ionic, atomic, and molecular fragment emission spectra from the plasma. In certain instances, the detector may include a charge-coupled device (CCD). In some cases, the CCD is an intensified CCD (ICCD). In certain cases, the detector further includes collection optics configured to direct emissions from the plasma to the detector. The collection optics may include reflective and/or semi-reflective collection optics, such as, but not limited to, a mirror (M), a beam splitter (BS), a polarizing beam splitter (PBS), and the like.

EXAMPLES

The following examples describe exemplary embodiments of the invention, and are not intended to limit the claimed invention.

Ablation Configuration

The LIBS probe comprised a Q-switched Nd:YAG laser CFR 200 (Quantel) that can deliver up to 300 mJ per pulse at a wavelength of 1064 nm. The pulse duration was about 9 ns FWHM at a repetition rate is 5 Hz. The laser energy was adjusted to about 125 mJ. Under these conditions, the estimated spot diameter on the surface of the samples was about 600 am, which yields a laser fluence of about 40 J/cm². The light emitted by the plasma passed through the center of a dichroic mirror positioned next to the plasma expansion direction and was then focused onto the entrance of an optical fiber bundle by an achromatic lens. The optical fiber bundle (comprising 14 individual fibers of 100 am core diameter), which guides the light break out into two legs (7 aligned optical fiber each) at the end. The two outputs were connected to the two entrances of a dual channel spectrometer (Avantes). The channel 1 was a 75 mm Czerny-Turner type UV/VIS spectrometer with a covered spectral range of approx. 230 nm to 458 nm using a linear CCD detector with 2048 elements. The chosen configuration leads to a linear dispersion of 19 nm/mm (i.e. 270 μm per pixel of 14 μm width). The channel 2 is a VIS/NIR spectrometer with a covered spectra range of 460 to 920 nm (VIS/NIR). In addition, an air knife was positioned next to the sample to provide a reasonably clean atmosphere (i.e. free of aerosols) for the next laser shot. An argon flow gas is used to keep an inert controlled atmosphere in order to avoid the contributions of atmospheric gases to the emission spectra.

A computer-controlled translation stage with three moveable axes was used to support the sample holder to change the position of the laser ablation site as required.

Signal Processing

The experimental set-up and spectral data were controlled using custom applications developed in LabVIEW 2012 (National Instruments, Austin, Tex., USA). Custom algorithms for pre-processing processing under Matlab2014b environment (The MathWorks Inc., Natick, Mass., USA) have been developed. This procedure disregarded the less significant spectra of poor quality/intensity. In addition, spectral data pre-processing and chemometrics were performed using OPUS™ software (Bruker Ltd, Milton, Calif.). Optimization routines within the OPUS™ software can be used to help identify spectral regions and spectral pre-processing techniques that are the most useful for reducing the root mean square errors of cross validation for the calibration samples.

Oil Sands Samples

Testing was performed on 40 samples with wide sample variety of composition where the bitumen/water/solids content were determined by Dean-Stark extraction method and the particle size distribution by Coulter Laser diffraction. Up to 10 of those samples were test set validation samples that were not used in the calibration model. For each sample, the surface was flattened with a glass surface. To overcome the heterogeneity of the sample, a moveable sample holder was used to scan the target. To go to the depth of the material, the surface was scanned multiple times. Three thousand laser shots, each with a spot size of 600 μm were used to ablate a square-shaped crater about 5 mm×5 mm to a depth of 4 mm. A total of 5 craters were ablated per sample for a total ablated volume of 0.5 cm³ per sample.

Figure 2A:
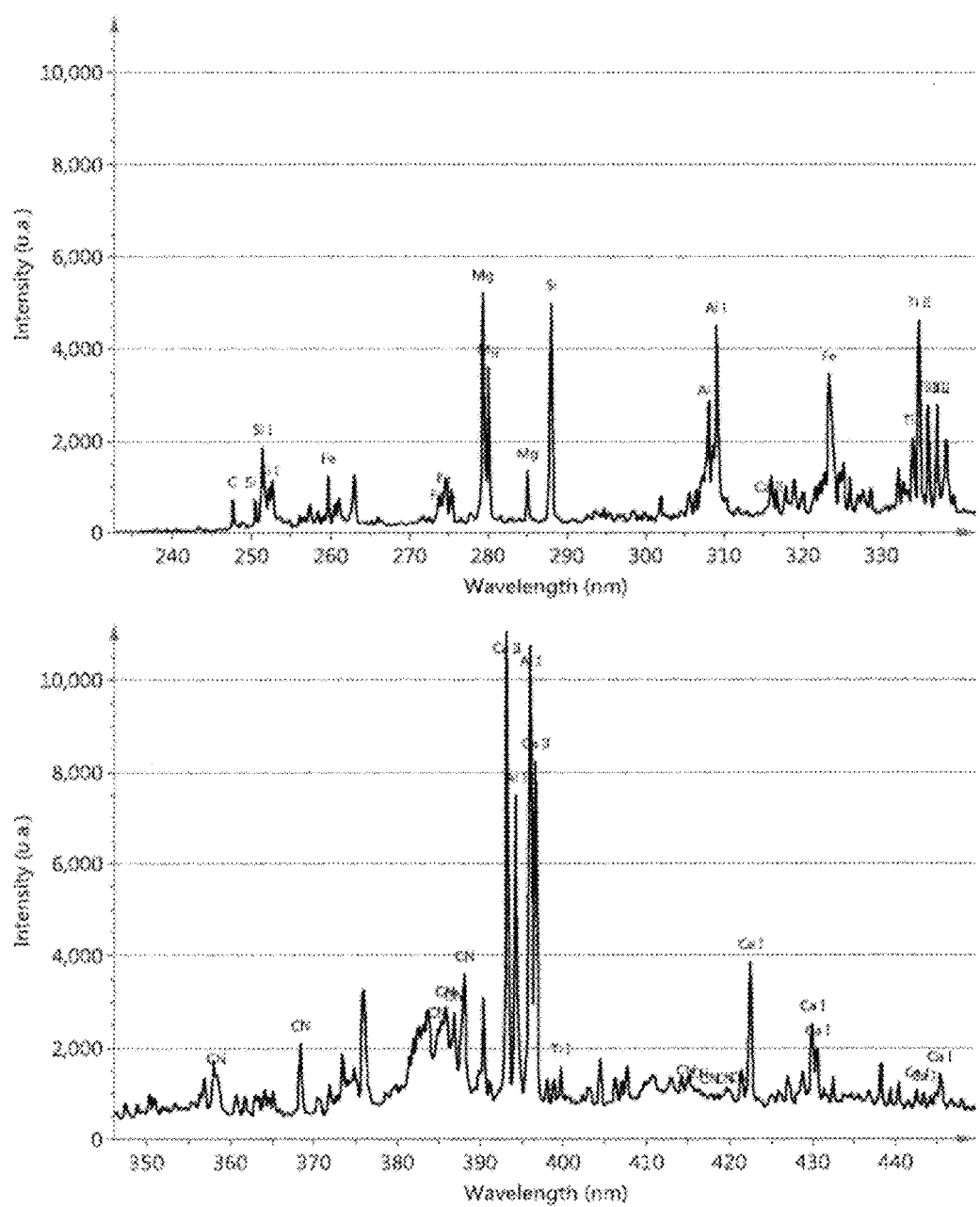
FIGS. 2A and 2B shows an emission spectrum which is the average of a plurality of spectra obtained in four different spectral windows.
Figure 2B:
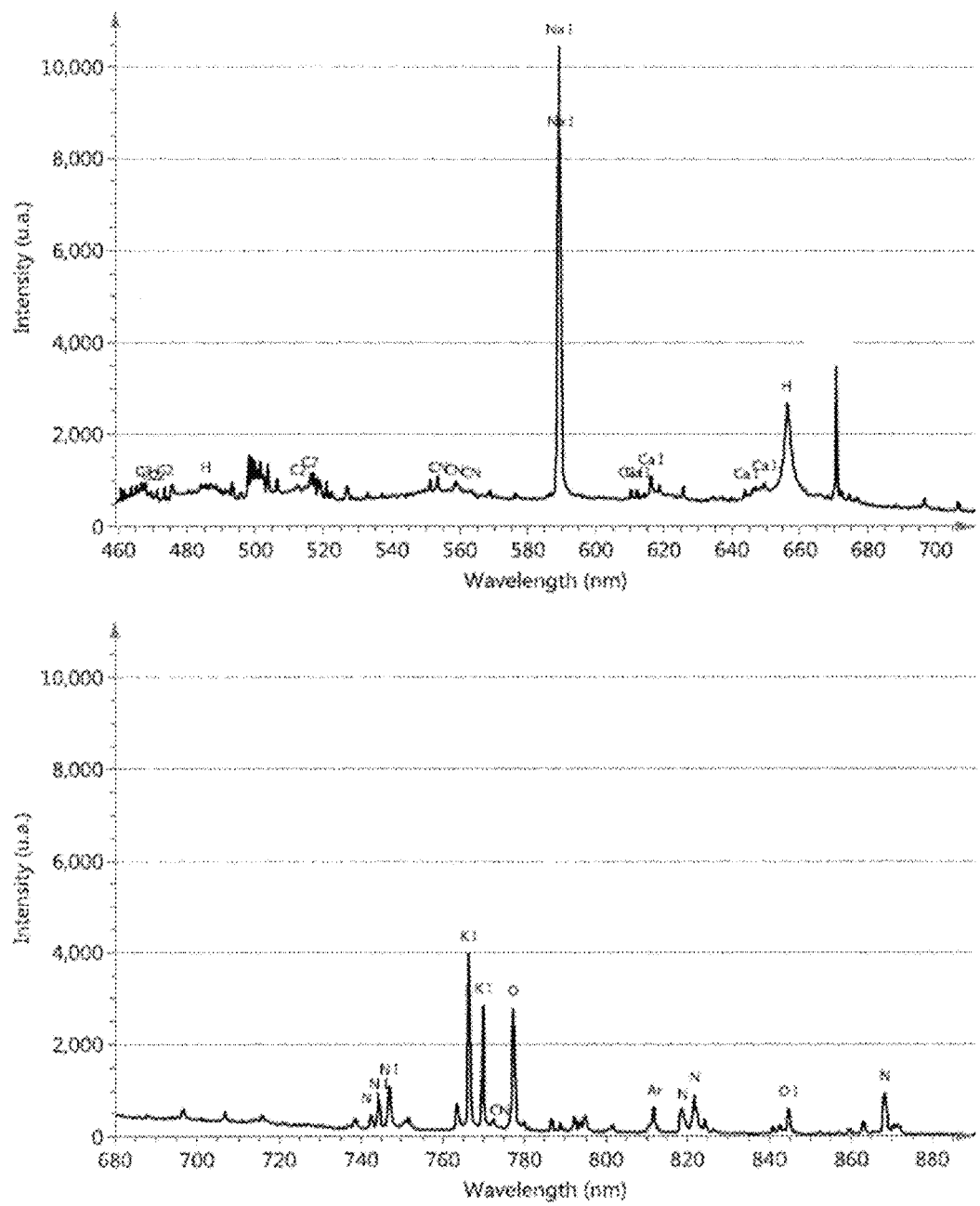

The spectra from all of the samples were averaged and are shown in FIGS. 2A and 2B. Spectral lines for some elements (e.g. H, C, N, Ca, Mg, K, Si, Al, Fe, Ti) and molecular fragments (e.g. CN and $C_2$) of interest are visible.

Quantitative Analysis

This section describes certain chemometric models developed to determine the composition and properties of the oil sands samples. The results presented in this section are obtained using a calibration set of up to 30 calibration samples. Calibration samples were used to identify the best spectral preprocessing and spectral region selections for PLS modelling for a given parameter (e.g. % bitumen content) with the aid of the commercially-available OPUS™ software (Bruker Ltd, Milton, Calif.). Up to 10 test set samples that were not used in the calibration are predicted and then compared to reference values. The root mean square error of predictions (RMSEP) were calculated from the test set results to evaluate the accuracy of the measurement.

Figure 3:
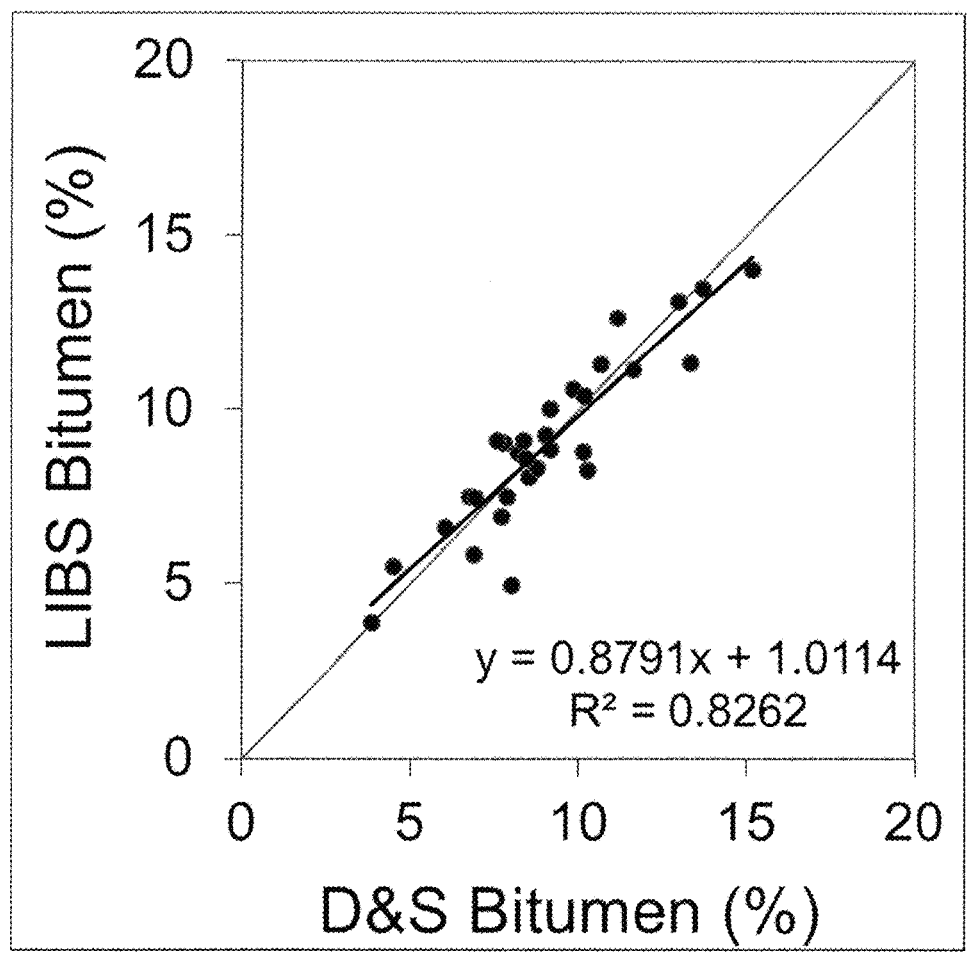
FIG. 3 shows the LIBS % bitumen cross-validation results versus the Dean-Stark % bitumen reference results for the calibration samples used to create the chemometric PLS calibration loadings.
Figure 4:
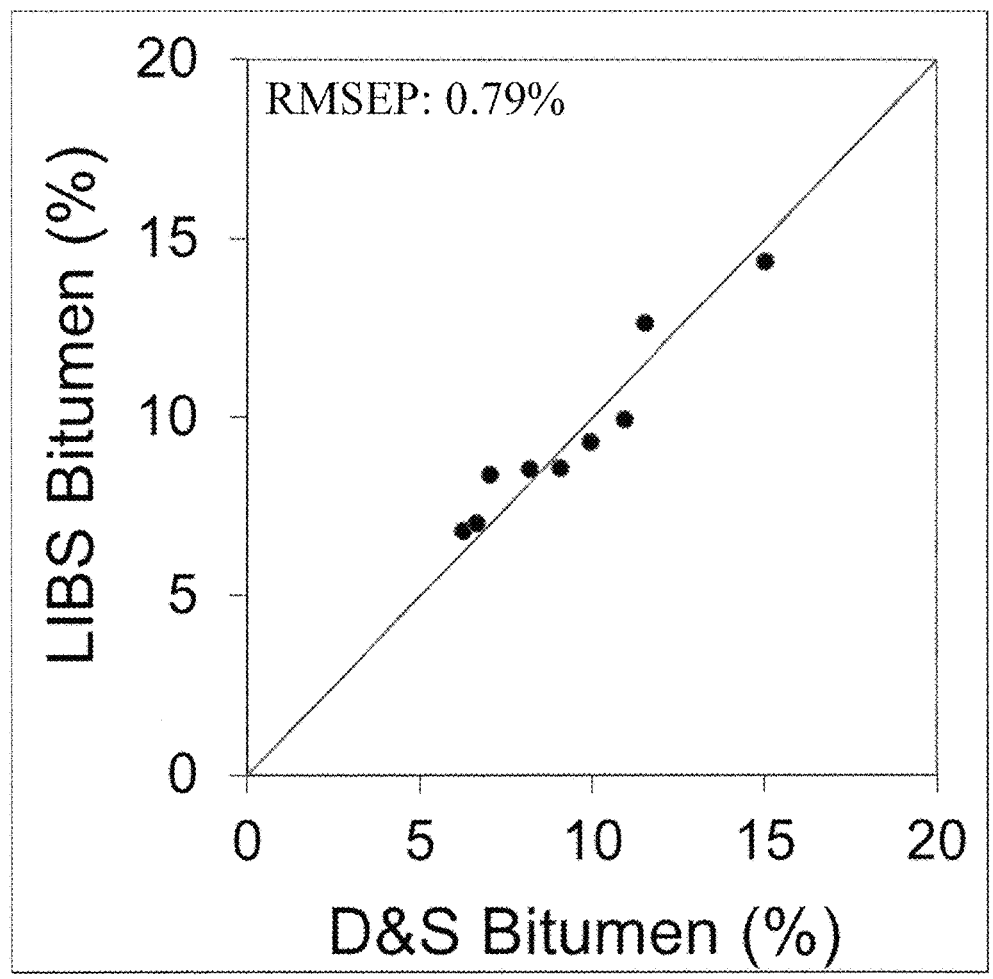
FIG. 4 shows the LIBS % bitumen content versus Dean-Stark reference concentrations for test set validation samples that were not used in the calibration model.

FIG. 3 shows the cross-validation LIBS % bitumen content in the oil sand sample versus Dean-Stark reference concentrations for the calibration samples following specific spectral region selection, Mean Centering, and Standard Normal Variate (SNV) preprocessing, resulting in a PLS model with a rank of 6. FIG. 4 shows the test set validation LIBS % bitumen content versus the Dean-Stark reference values with a RMSEP of 0.79%.

Figure 5:
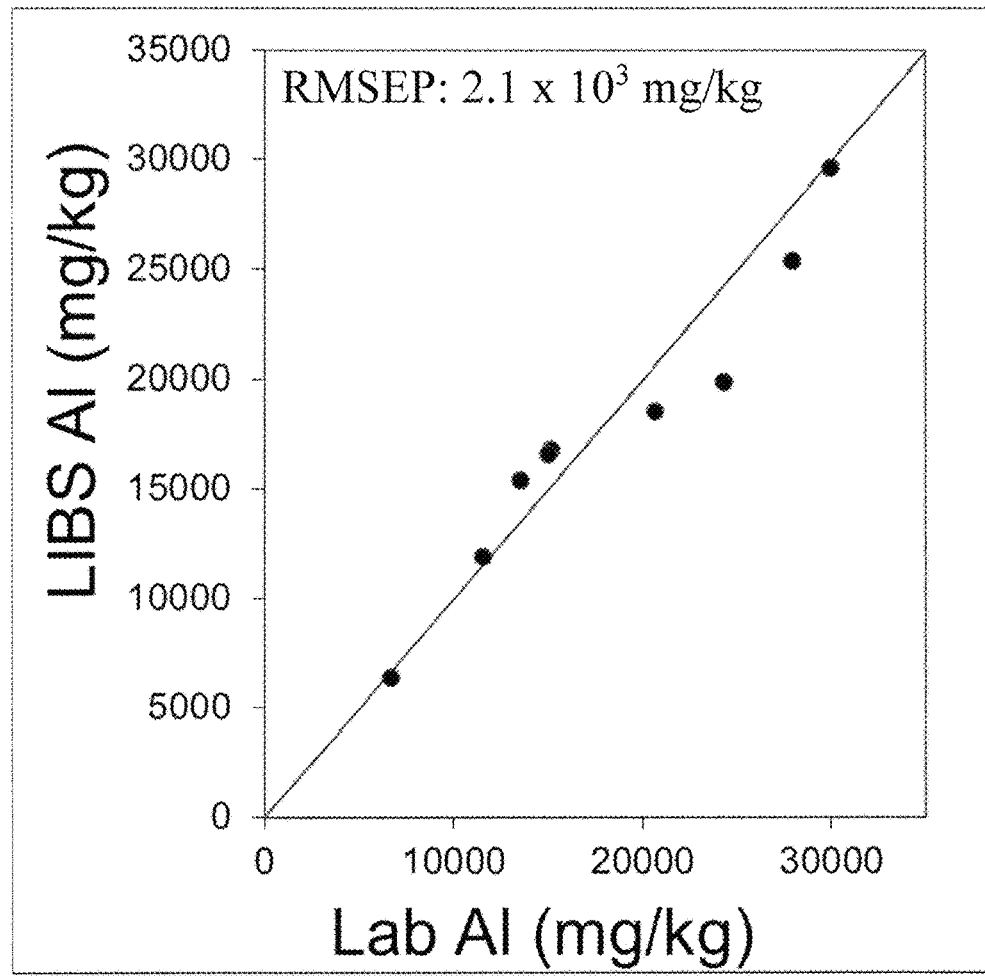
FIG. 5 shows the LIBS aluminum content versus the reference content for test set validation samples that were not used in the calibration model.

FIG. 5 shows the LIBS test set validation aluminum content versus reference values (RMSEP of $2.1 \times 10^3$ mg/kg). Spectral preprocessing: Mean Centering and Standard Normal Variate (SNV). Chemometric calibration: selected spectral regions from 29 well-characterized calibration samples were modelled with PLS producing a model with a rank of 2.

Figure 6:
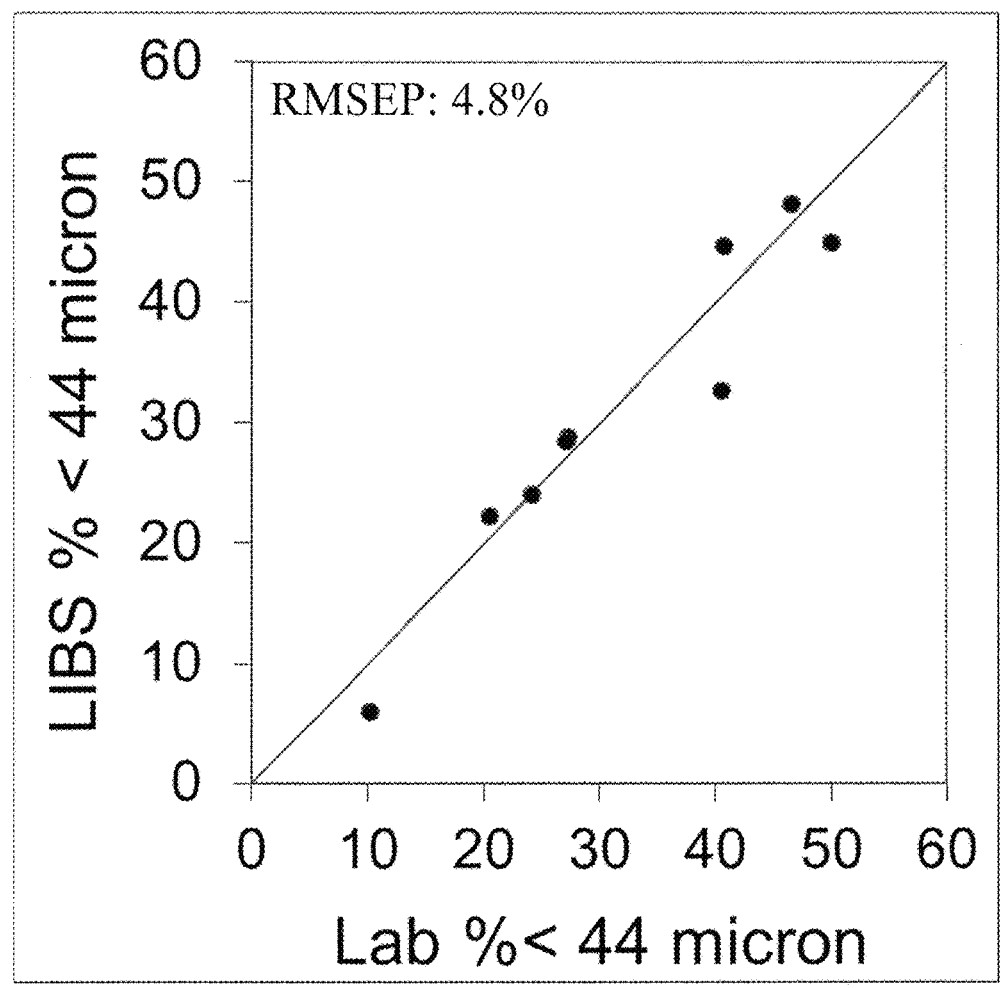
FIG. 6 shows the LIBS % fine particles <44 μm content in the whole sample (not just solids) versus the reference content for test set validation samples that were not used in the calibration model.

FIG. 6 shows the LIBS test set validation fine particle (<44 µm) content in the whole sample (not just solids) versus reference values (RMSEP 4.8%). Spectral preprocessing: Mean Centering and Standard Normal Variate (SNV). Chemometric calibration: selected spectral regions from 29 well-characterized calibration samples were modelled with PLS producing a model with a rank of 2.

Figure 7:
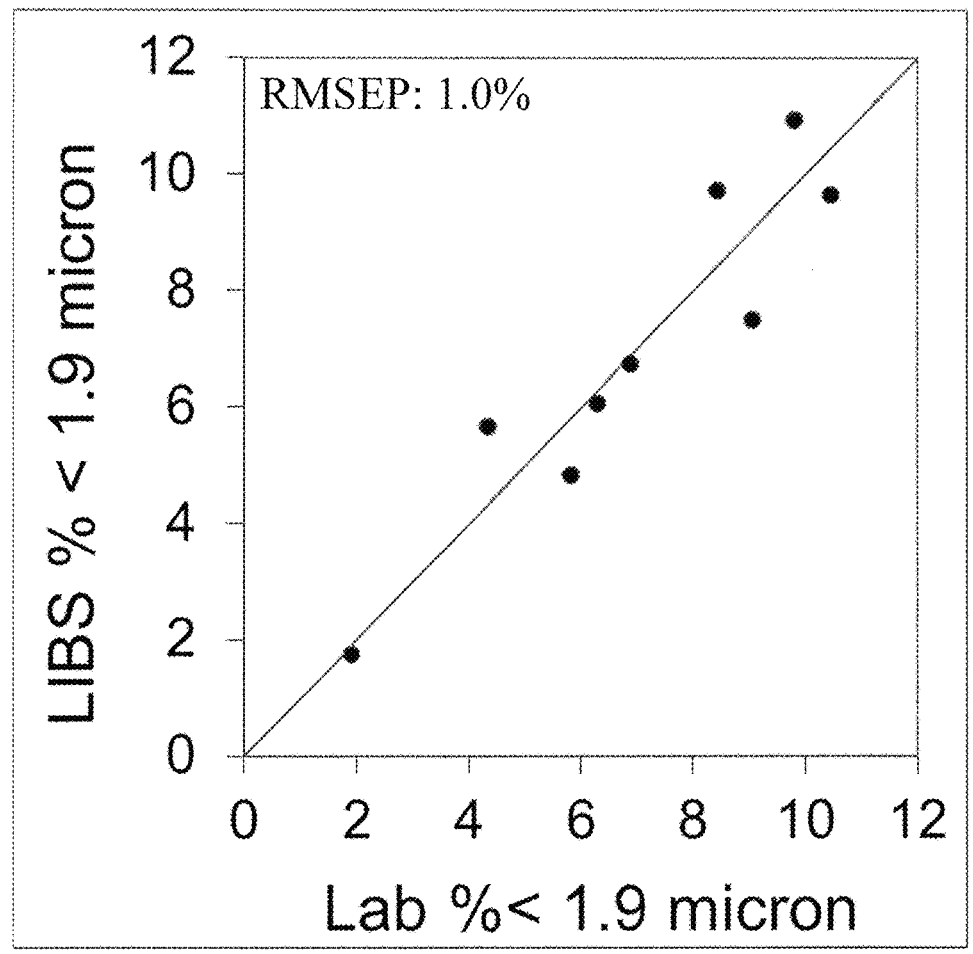
FIG. 7 the LIBS % fine particles <1.9 μm content in the whole sample (not just solids) versus the reference content for test set validation samples that were not used in the calibration model.

FIG. 7 shows the LIBS test set validation fine particle (<1.9 µm) content in the whole sample (not just solids) versus reference values (RMSEP 1.0%). Spectral preprocessing: Mean Centering and Standard Normal Variate (SNV). Chemometric calibration: selected spectral regions from 29 well-characterized calibration samples were modelled with PLS producing a model with a rank of 2.

Figure 8:
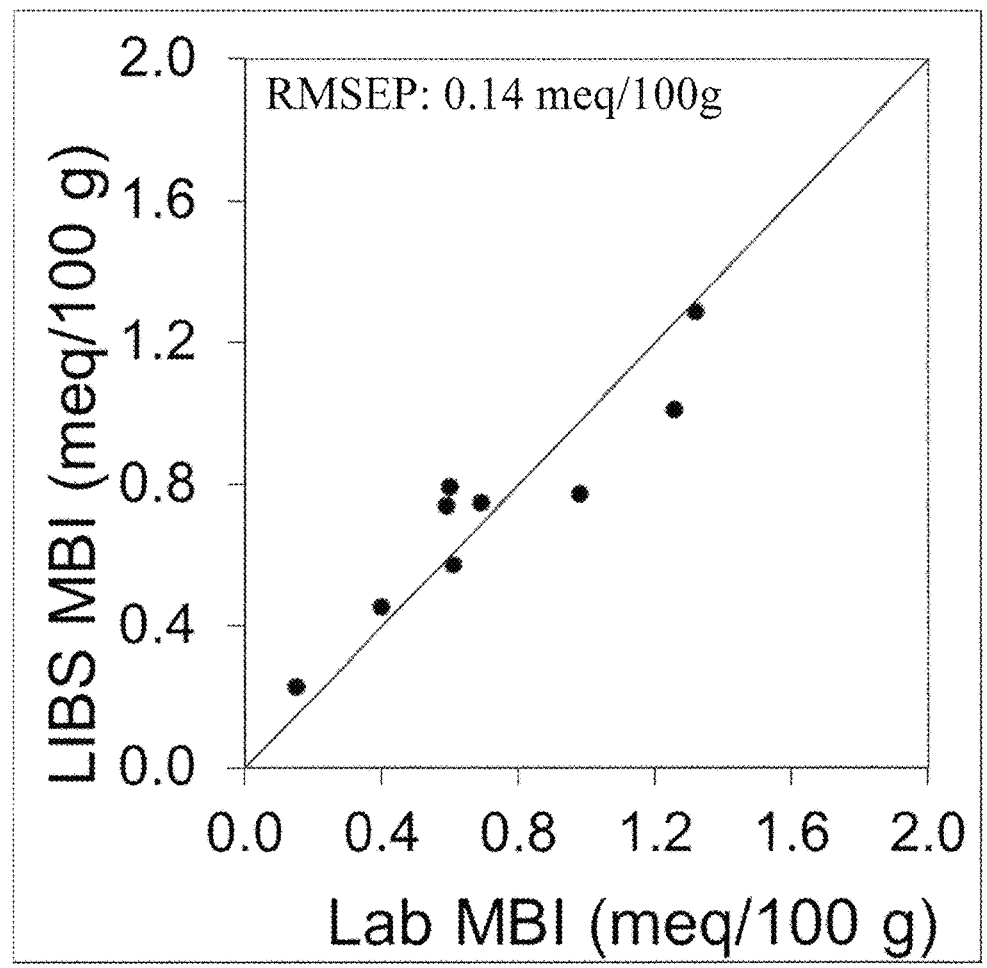
FIG. 8 shows the LIBS MBI values in the whole sample (not just solids) versus the reference values for test set validation samples that were not used in the calibration model.

FIG. 8 shows the LIBS test set validation of methylene blue index in meq per total amount of sample (not just solids) versus reference values (RMSEP: 0.14 meq/100 g). Spectral preprocessing: Mean Centering and First Derivative. Chemometric calibration: selected spectral regions from 29 well-characterized calibration samples were modelled with PLS producing a model with a rank of 1.

Figure 9:
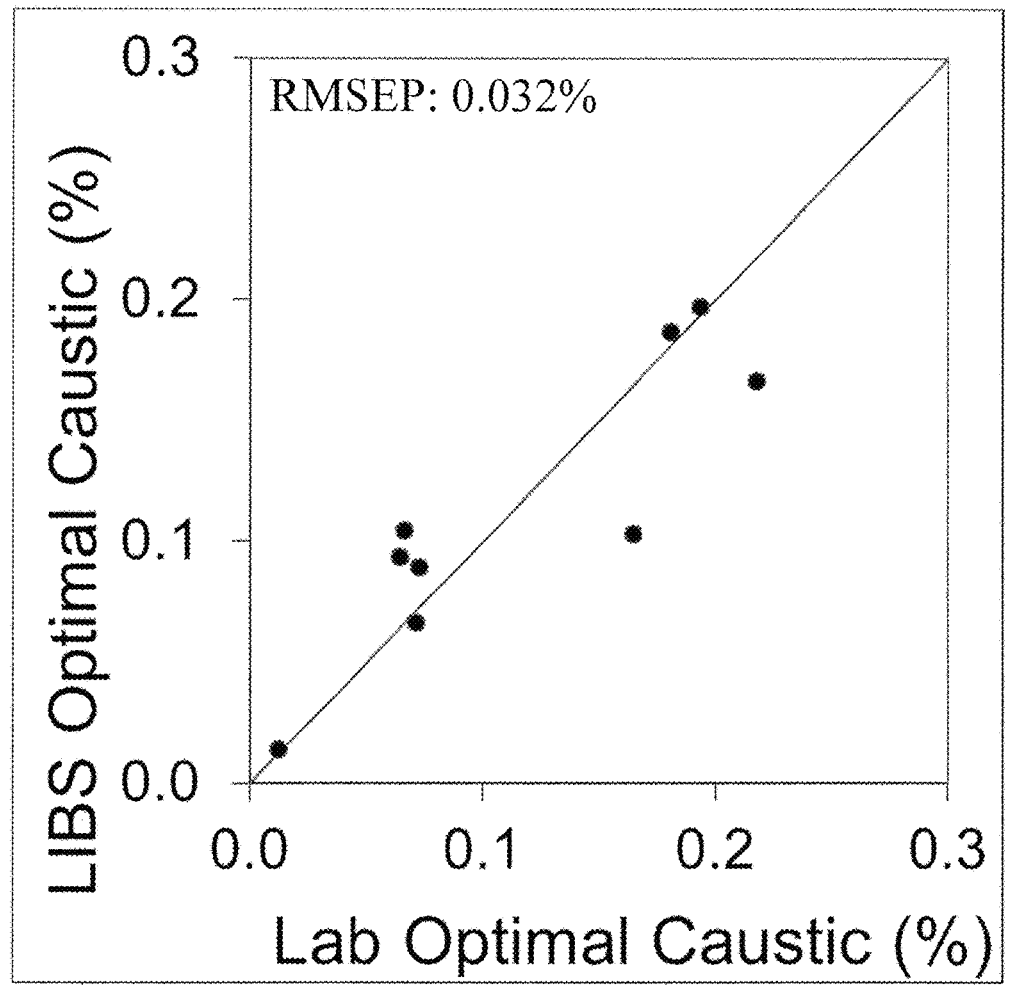
FIG. 9 shows the LIBS % optimal caustic dose as a percentage of dry oil sand weight versus the reference values for test set validation samples that were not used in the calibration model.

FIG. 9 shows the LIBS test set validation optimal amount of caustic (wt % caustic per weight of oil sands) to achieve maximum batch extraction unit (BEU) bitumen recovery under a given set of conditions versus reference values (RMSEP: 0.032%). Spectral preprocessing: Mean Centering and Multiplicative Scatter Correction. Chemometric calibration: selected spectral regions from 29 well-characterized calibration samples were modelled with PLS producing a model with a rank of 6.

Figure 10:
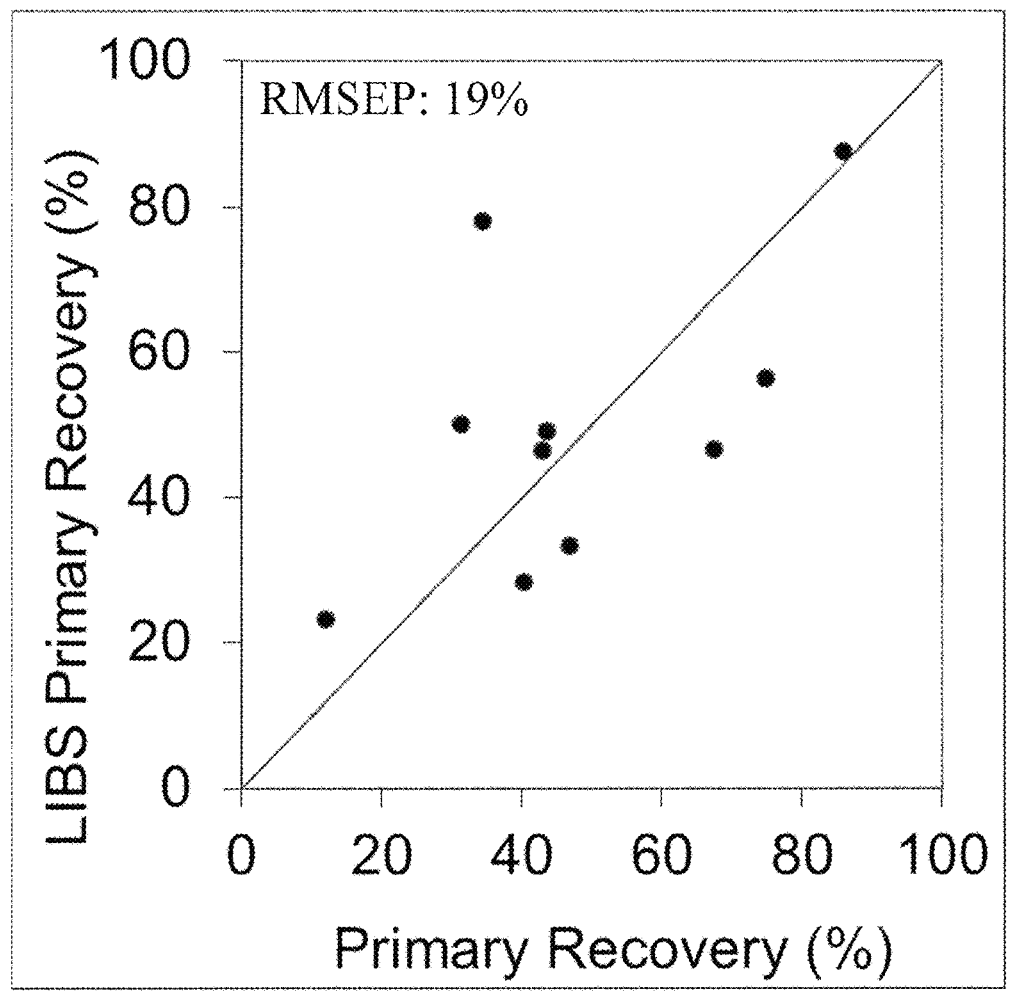
FIG. 10 shows the LIBS % primary bitumen recovery values in the primary froth produced in the batch extraction unit (BEU) under a given set of conditions, versus the laboratory measured primary recovery for test set validation samples that were not used in the calibration model. This is one example of predicting bitumen recovery for a given set of BEU operating conditions directly from oil sands ore LIBS spectra.

FIG. 10 shows the LIBS test set validation % bitumen recovery values in the primary froth produced in the batch extraction unit (BEU) under a given set of conditions, versus laboratory-measured primary recovery (RMSEP: 19%). Spectral preprocessing: Mean Centering and Standard Normal Variate (SNV). Chemometric calibration: selected spectral regions from 30 well-characterized calibration samples were modelled with PLS producing a model with a rank of 4.

Figure 11:
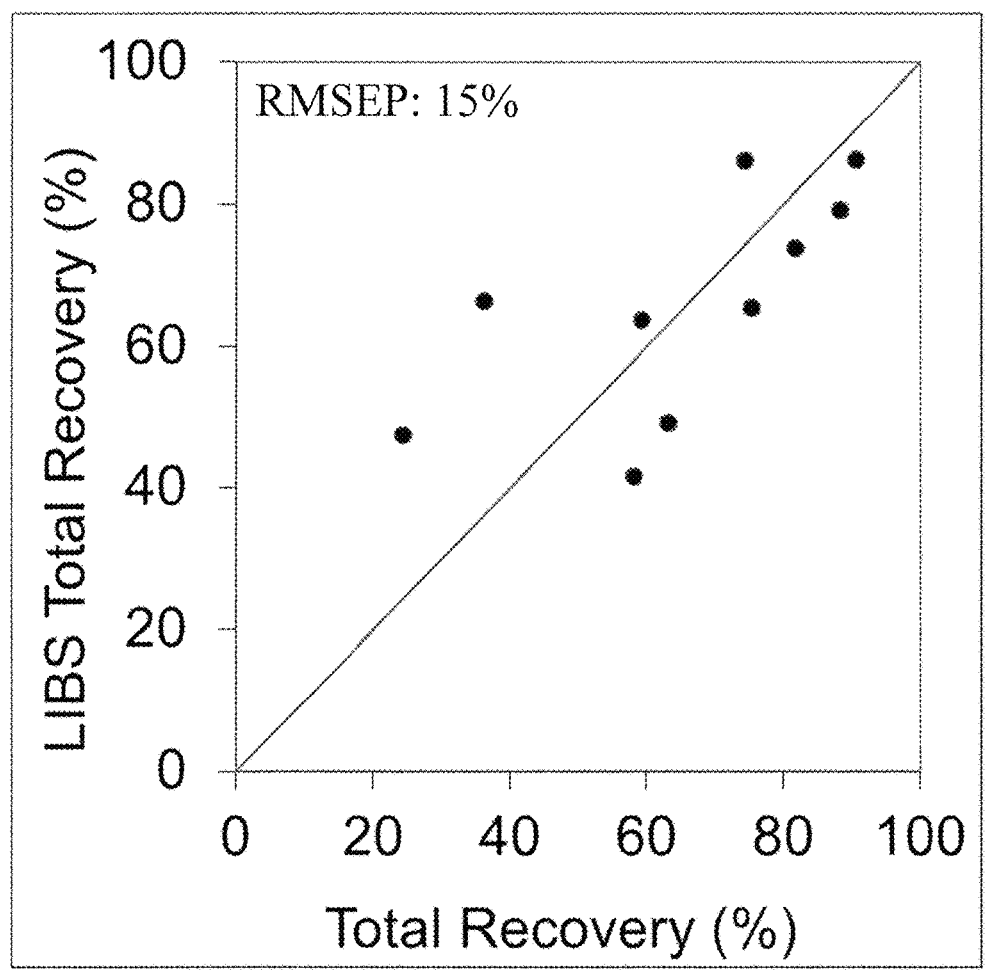
FIG. 11 shows the LIBS % bitumen recovered in the combined primary and secondary froths produced in the BEU under a given set of conditions, versus the laboratory measured bitumen total recovery for test set validation samples that were not used in the calibration model. This is one example of predicting bitumen recovery for a given set of BEU operating conditions directly from oil sands ore LIBS spectra.

FIG. 11 shows the LIBS test set validation % bitumen recovered in the combined primary and secondary froths produced in the BEU under a given set of conditions, versus laboratory measured bitumen total recovery values (RMSEP: 15%). Spectral preprocessing: First Derivative and Standard Normal Variate (SNV). Chemometric calibration: selected spectral regions from 30 well-characterized calibration samples were modelled with PLS producing a model with a rank of 5.

Figure 12:
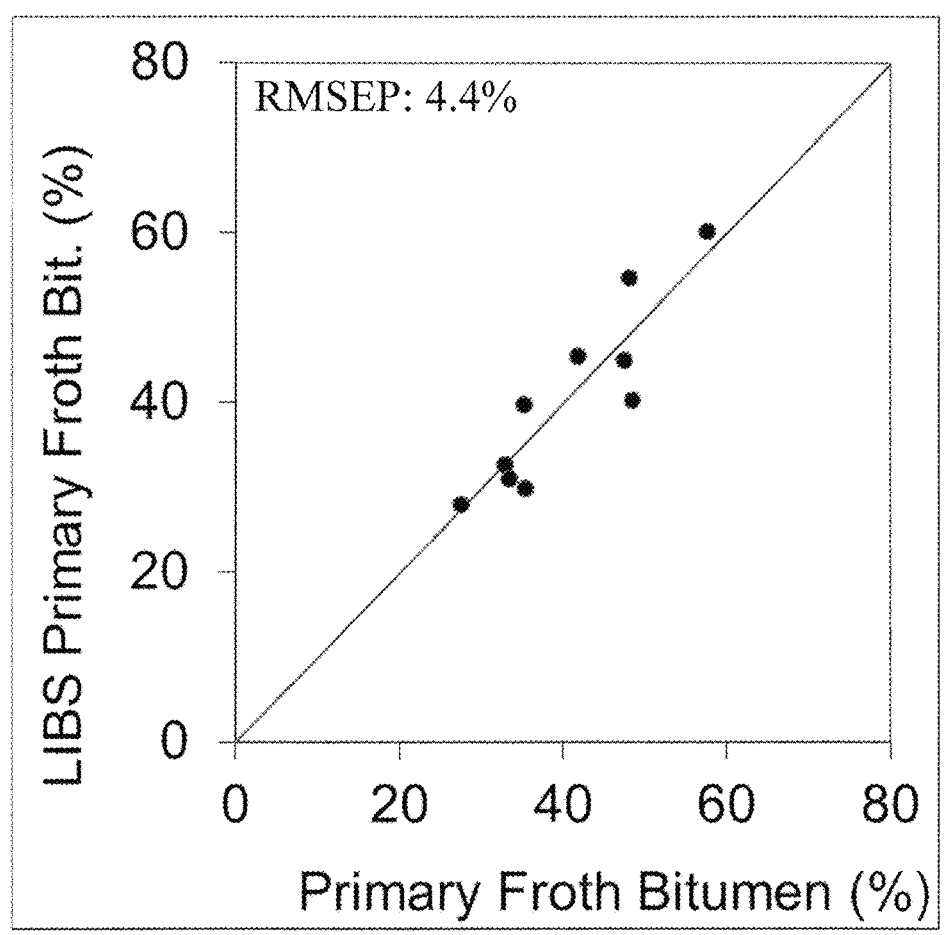
FIG. 12 shows the LIBS % bitumen in the primary froth produced in the BEU under a given set of conditions, versus the laboratory measured primary froth bitumen % for test set validation samples that were not used in the calibration model. This is one example of predicting bitumen froth quality for a given set of BEU operating conditions directly from oil sands ore LIBS spectra.

FIG. 12 shows the LIBS test set validation % bitumen content in the primary froth produced in the BEU under a given set of conditions, versus the laboratory measured primary froth % bitumen (RMSEP 4.4%). Spectral preprocessing: Standard Normal Variate (SNV). Chemometric calibration: selected spectral regions from 30 well-characterized calibration samples were modelled with PLS producing a model with a rank of 4.

Figure 13:
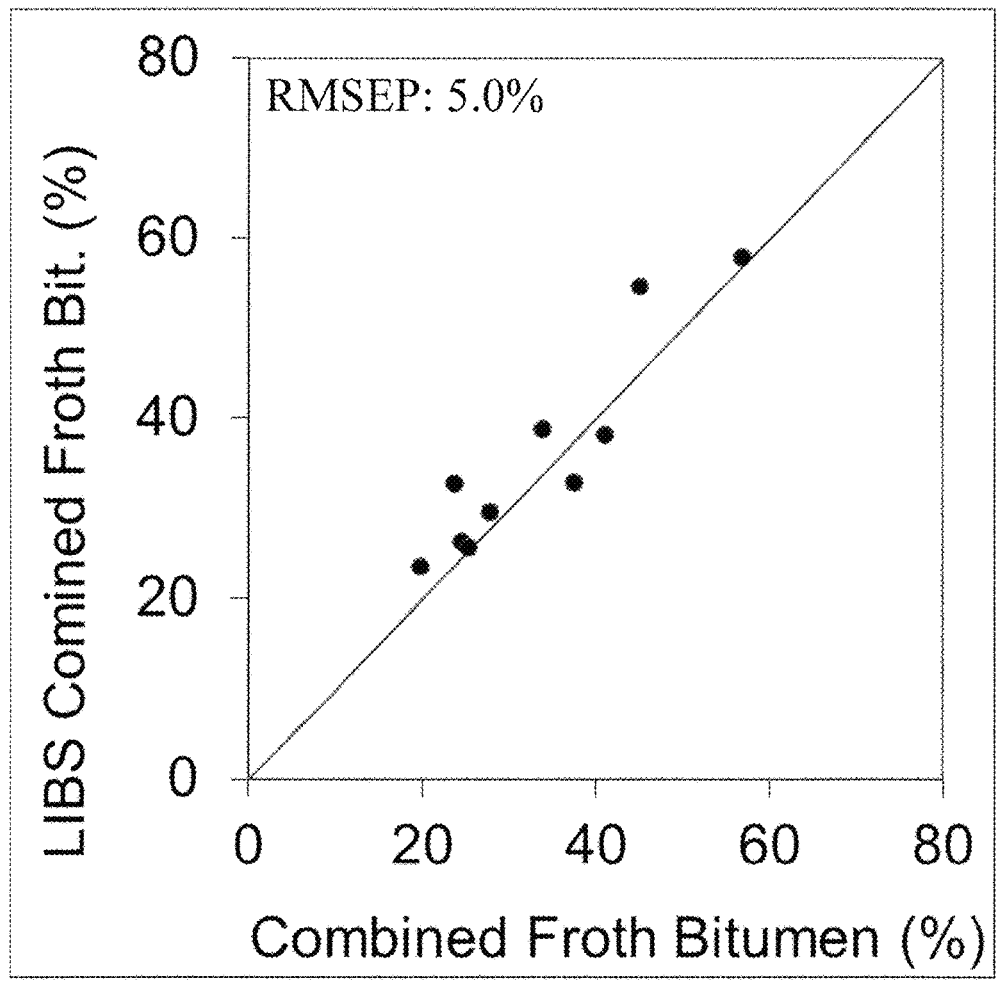
FIG. 13 shows the LIBS % bitumen in the combined primary and secondary froths produced in the BEU under a given set of conditions, compared to laboratory measured combined froth bitumen % for test set validation samples that were not used in the calibration model. This is one example of predicting bitumen froth quality for a given set of BEU operating conditions directly from oil sands ore LIBS spectra.

FIG. 13 shows the LIBS test set validation % bitumen content in the combined primary and secondary froths produced in the BEU under a given set of conditions, compared to laboratory measured combined froth % bitumen values (RMSEP: 5.0%). Spectral preprocessing: Multiplicative Scatter Correction. Chemometric calibration: selected spectral regions from 30 well-characterized calibration samples were modelled with PLS producing a model with a rank of 3.

Figure 14:
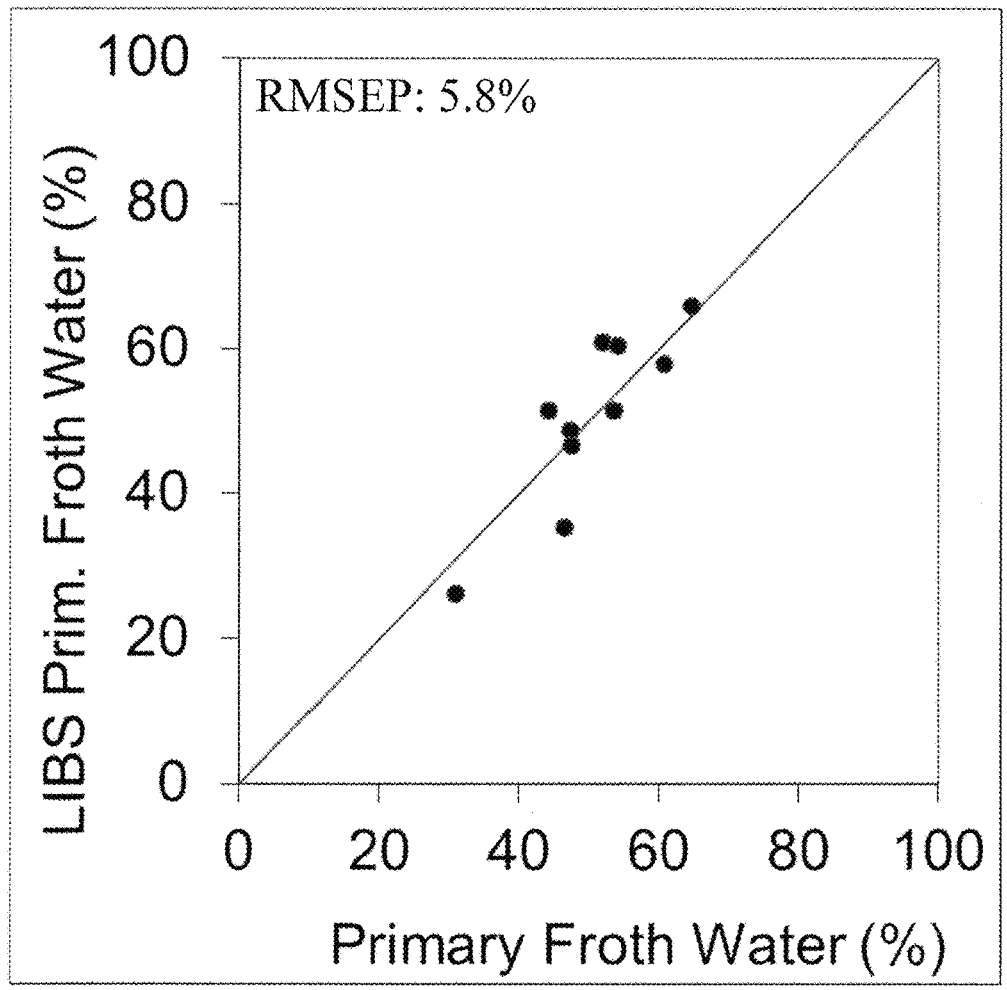
FIG. 14 shows the LIBS % water in the primary froth produced in the BEU under a given set of conditions, versus the actual measured primary froth water % for test set validation samples that were not used in the calibration model. This is one example of predicting bitumen froth quality for a given set of BEU operating conditions directly from oil sands ore LIBS spectra.

FIG. 14 shows the LIBS test set validation % water in the primary froth produced in the BEU under a given set of conditions, versus the laboratory measured primary froth % water content (RMSEP: 5.8%). Spectral preprocessing: Standard Normal Variate (SNV). Chemometric calibration: selected spectral regions from 30 well-characterized calibration samples were modelled with PLS producing a model with a rank of 4.

Figure 15:
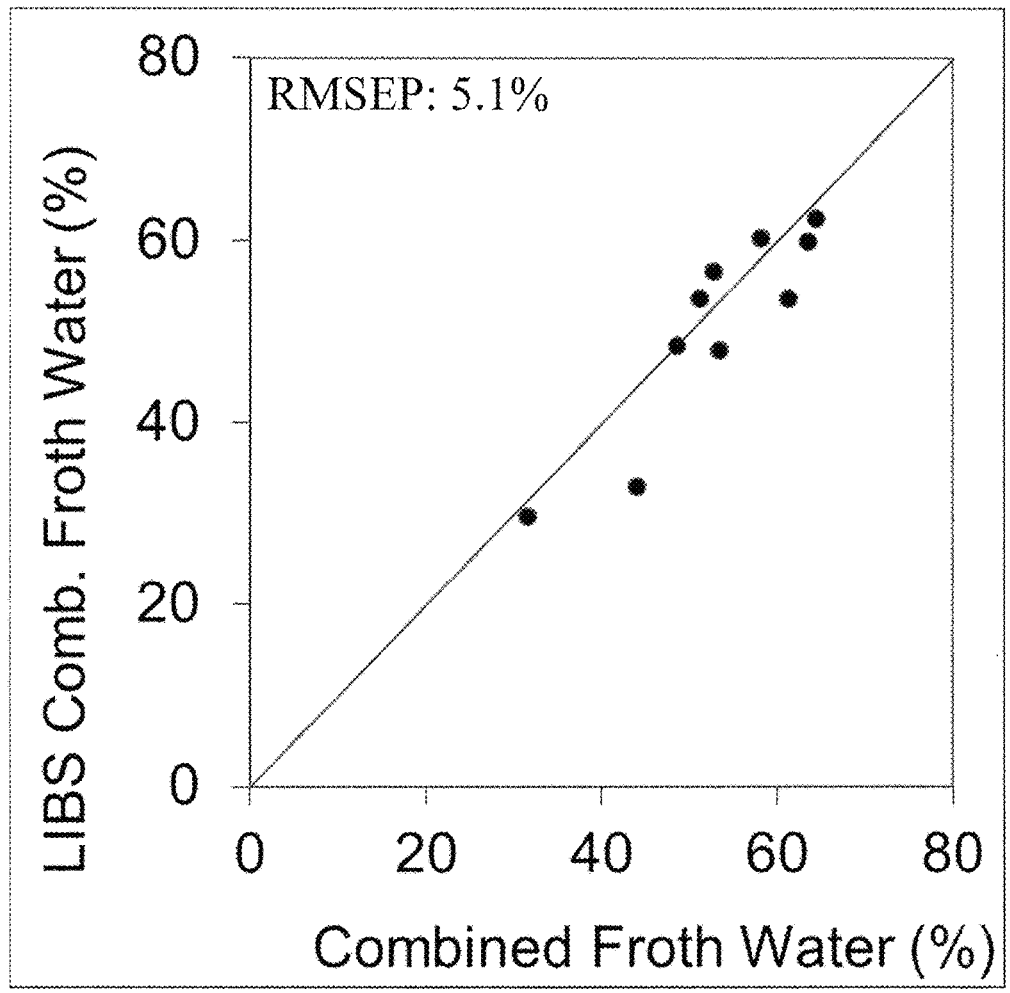
FIG. 15 shows the LIBS % water in the combined primary and secondary froths produced in the BEU under a given set of conditions, versus the laboratory measured combined froth water % for test set validation samples that were not used in the calibration model. This is one example of predicting bitumen froth quality for a given set of BEU operating conditions directly from oil sands ore LIBS spectra.

FIG. 15 shows the LIBS test set validation % water in the combined primary and secondary froths produced in the BEU under a given set of conditions, versus the laboratory measured combined froth % water content (RMSEP 5.1%). Spectral preprocessing: Multiplicative Scatter Correction. Chemometric calibration: selected spectral regions from 30 well-characterized calibration samples were modelled with PLS producing a model with a rank of 3.

Figure 16:
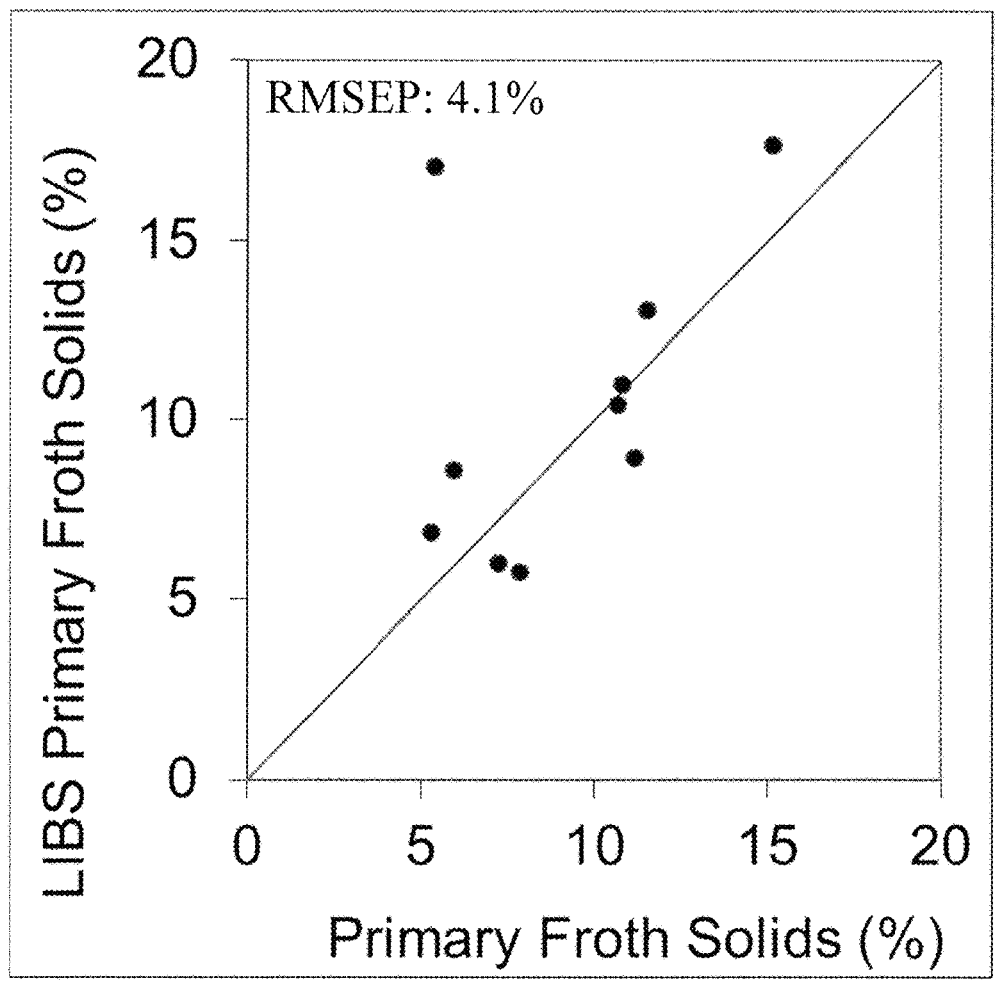
FIG. 16 shows the LIBS % solids in the primary froth produced in the BEU under a given set of conditions, versus the laboratory measured primary froth solids % for test set validation samples that were not used in the calibration model. This is one example of predicting bitumen froth quality for a given set of BEU operating conditions directly from oil sands ore LIBS spectra.

FIG. 16 shows the LIBS test set validation of % solids in the primary froth produced in the BEU under a given set of conditions, versus the laboratory measured primary froth % solids content (RMSEP: 4.1%). Spectral preprocessing: Mean Centering and Standard Normal Variate (SNV). Chemometric calibration: selected spectral regions from 30 well-characterized calibration samples were modelled with PLS producing a model with a rank of 10.

Figure 17:
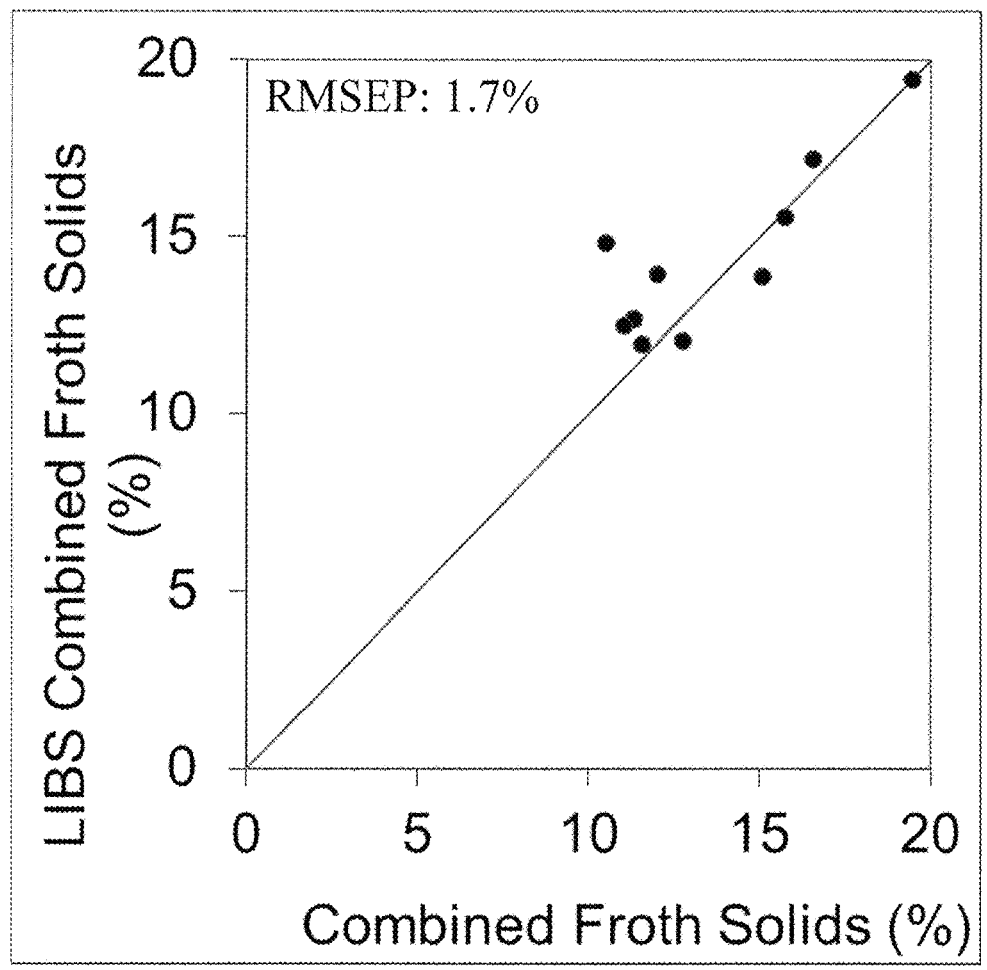
FIG. 17 shows the LIBS % solids in the combined primary and secondary froths produced in the BEU under a given set of conditions, versus the laboratory measured combined froth solids % for test set validation samples that were not used in the calibration model. This is one example of predicting bitumen froth quality for a given set of BEU operating conditions directly from oil sands ore LIBS spectra.
Figure 18:
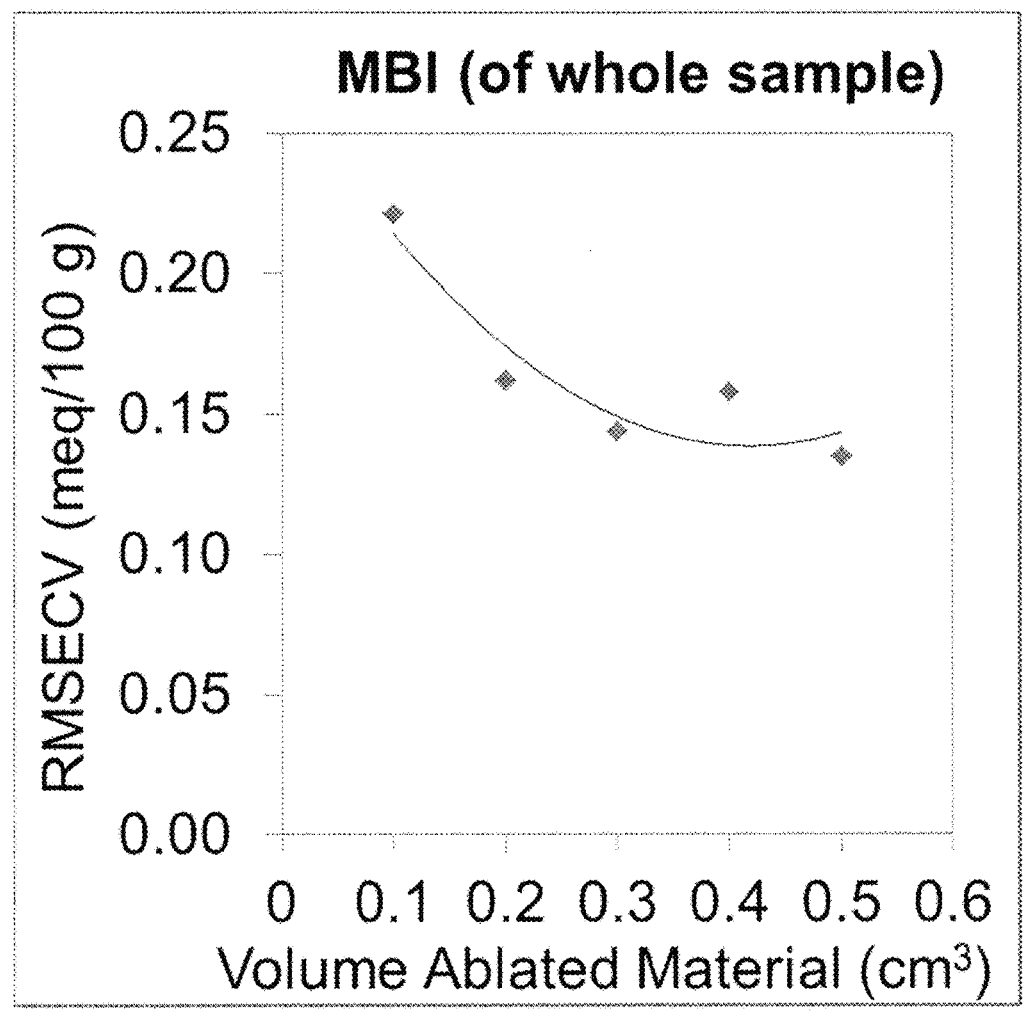
FIG. 18 shows the root mean square error of cross validation for MBI (of whole sample) as a function of total sample volume ablated from averaging the spectra from 1 to 5 laser ablation sites together (~4 mm sampling depth achieved at each ablation site).
Figure 19:
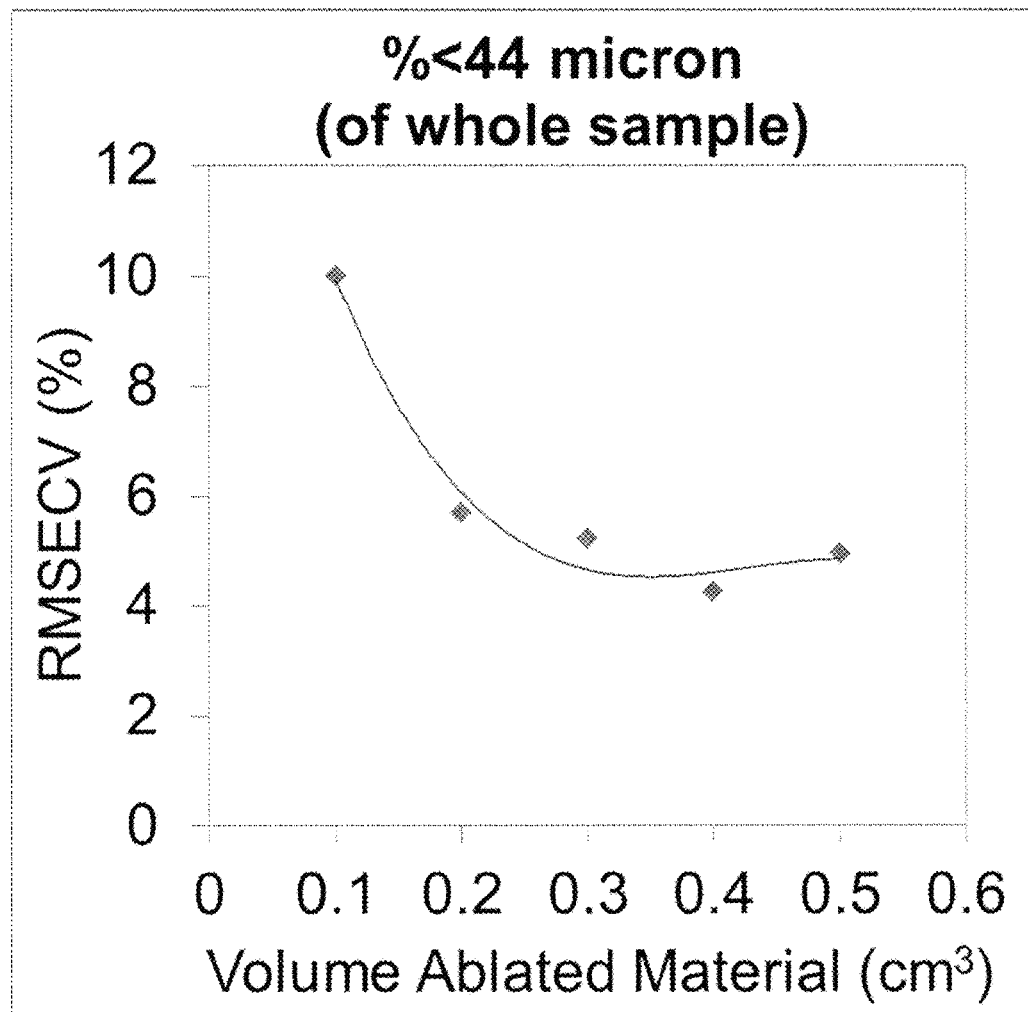
FIG. 19 shows the root mean square error of cross validation for %<44 micron content (of whole sample) as a function of total sample volume ablated from averaging the spectra from 1 to 5 laser ablation sites together (~4 mm sampling depth achieved at each ablation site).

FIG. 17 shows the LIBS test set validation % solids in the combined primary and secondary froths produced in the BEU under a given set of conditions, versus the laboratory measured combined froth % solids Content (RMSEP: 1.7%). Spectral preprocessing: Min-Max Range Scaling. Chemometric calibration: selected spectral regions from 30 well-characterized calibration samples were modelled with PLS producing a model with a rank of 5.

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

REFERENCES

Where permitted, the following references are incorporated herein by reference in their entirety, for all purposes.
1. B. K. Lavine and J. Workman, Analytical Chemistry, 2002, 74, 2763-2769.
2. J. Workman, Chemometrics and Intelligent Laboratory Systems, 2002, 60, 13-23.
3. J. El Haddad, L. Canioni, B. Bousquet, Spectrochimica Acta Part B: Atomic Spectroscopy, 2014, 101, 171-182.
4. C. D. Quarles, J. J. Gonzalez, L. J. East, J. H. Yoo, M. Morey and R. E. Russo, J. Anal. At. Spectrom., 2014, 29, 1238-1242.
5. C. Cortes and V. Vapnik, Mach. Learn., 1995, 20, 273-297.
6. P. Inakollu, T. Philip, A. K. Rai, F. Y. Yueh and J. P. Singh, Spectrochim. Acta, Part B, 2009, 64, 99-104.
7. J. B. Sirven, B. Bousquet and L. Canioni, Anal. Bioanal. Chem., 2006, 385, 256-262.
8. F. Anabitarte, J. Mirapeix, 0. M. C. Portilla, J. M. Lopez Higuera and A. Cobo, IEEE Sens. J., 2012, 12, 64-70.9. Y. Yu, L. Guo, Z. Hao, X. Li, M. Shen, Q. Zeng, K. Li, X. Zeng, Y. Lu and Z. Ren, Opt Express, 2014, 22, 3895-3901.
9. K. E. Washburn, Organic Geochemistry, 2015, 83-84,114-117.
11. Sanford, E. C., Seyer, F. A., "Processability of Athabasca Tar Sand Using A Batch Extraction Unit: The Role of NaOH," Canadian Mining & Metallurgical Bulletin (CIM Magazine), Vol. 72, Issue 803, March 1979, 164-169.

What is claimed is:

1. A method of determining at least one property of interest of a test oil sands ore sample, comprising the steps of:
    (a) applying a plurality of pulsed laser shots focused on a surface of the test oil sand ore sample to ablate the test oil sands ore sample and create a plurality of short-lived plasmas;
    (b) acquiring the emission spectra from at least some or all of the plasmas;
    (c) repeating steps (a) and (b) on one or more ablation sites until a predetermined minimum ablation depth and total ablation volume have been achieved;
    (d) averaging the acquired emission spectra together for the test oil sands ore sample to form a test emission spectrum;
    (e) optionally, preprocessing the test emission spectrum; and
    (f) applying at least one calibration loading to determine the at least one property of interest, wherein the at least one calibration loading is obtained from a chemometric model relating an emission spectrum, or a portion of an emission spectrum, obtained from a known oil sands ore sample to a reference value obtained from a physicochemical analysis method for determining the at least one property of interest of the known oil sands ore sample;
    provided that the test or known oil sands ore sample is not an aqueous oil sands slurry; and
    provided that the at least one property of interest measured chemometrically from acquired LIBS spectra comprises one or more of the following,
    (a) properties related to oil sand bitumen extraction characteristic(s), comprising one or more of:
        1. Primary bitumen recovery
        2. Combined primary and secondary bitumen recovery
        3. Primary froth bitumen content
        4. Combined primary and secondary froth bitumen content
        5. Primary froth water content
        6. Combined primary and secondary froth water content
        7. Primary froth solids content
        8. Combined primary and secondary froth solids content
        9. Optimal process aid dosage (including but not limited to caustic); or
    (b) properties conventionally measured in a laboratory comprising either or both:
        10. Solids particle size information; or
        11. Solids methylene blue index;
    and not % bitumen content in the original oil sands ore or elemental concentrations.

2. The method of claim 1 wherein the minimum depth of each ablation site is about 4 mm, and the minimum total ablation volume from all ablation sites is about 0.3 cm$^3$.

3. The use of a laser induced breakdown plasma spectroscopic system comprising a laser ablator and a detector combined with one or more processors and a memory, wherein the memory stores machine-readable instructions that, when executed by the one or more processors, cause the system to carry out functions to implement the method of claim 1.

4. The method as claimed in claim 1, wherein the property measured is solids having a particle size less than 44 µm to determine optimal process aid dosage.

5. The method as claimed in claim 1, wherein the process aid is caustic.

* * * * *